United States Patent [19]
Hattersley et al.

[11] Patent Number: 5,902,785
[45] Date of Patent: May 11, 1999

[54] CARTILAGE INDUCTION BY BONE MORPHOGENETIC PROTEINS

[75] Inventors: Gary Hattersley, Cambridge; Neil M. Wolfman, Dover; Elisabeth A. Morris, Southboro; Vicki A. Rosen, Chestnut Hill, all of Mass.

[73] Assignee: Genetics Institute, Inc., Cambridge, Mass.

[21] Appl. No.: 08/646,193

[22] Filed: May 7, 1996

Related U.S. Application Data

[63] Continuation-in-part of application No. 08/467,110, Jun. 6, 1995, abandoned.

[51] Int. Cl.⁶ .......................... A61K 38/16; A61K 38/18
[52] U.S. Cl. ........................... 514/2; 514/8; 514/12
[58] Field of Search ........................ 514/2, 8, 12

[56] References Cited

U.S. PATENT DOCUMENTS

| | | | |
|---|---|---|---|
| 4,294,753 | 10/1981 | Urist | 260/112 R |
| 5,013,649 | 5/1991 | Wang et al. | 435/69.1 |
| 5,106,748 | 4/1992 | Wozney et al. | 435/252.3 |
| 5,108,922 | 4/1992 | Wang et al. | 435/365.1 |
| 5,116,738 | 5/1992 | Wang et al. | 435/69.1 |
| 5,141,905 | 8/1992 | Rosen et al. | 435/69.1 |
| 5,187,076 | 2/1993 | Wozney et al. | 435/69.1 |
| 5,364,839 | 11/1994 | Gerhart et al. | 514/12 |
| 5,520,923 | 5/1996 | Tija et al. | 424/426 |
| 5,658,882 | 8/1997 | Celeste et al. | 514/12 |

FOREIGN PATENT DOCUMENTS

| | | |
|---|---|---|
| WO 91/18098 | 11/1991 | WIPO . |
| WO 93/00432 | 1/1993 | WIPO . |
| WO 95/00050 | 1/1993 | WIPO . |
| 9316099 | 8/1993 | WIPO . |
| WO 94/26892 | 11/1994 | WIPO . |
| WO 94/26893 | 11/1994 | WIPO . |
| WO 95/01801 | 1/1995 | WIPO . |

OTHER PUBLICATIONS

Chang et al., J. Biol. Chem. 269(45):28227–28234 (1994).

*Primary Examiner*—Elizabeth Kemmerer
*Attorney, Agent, or Firm*—Steven R. Lazar; Barbara A. Gyure

[57] ABSTRACT

Compositions of proteins with cartilaginous tissue inducing and maintenance activity are disclosed. The compositions are useful in the treatment of osteoarthritis, cartilage defects and in related tissue repair.

6 Claims, No Drawings

5,902,785

CARTILAGE INDUCTION BY BONE MORPHOGENETIC PROTEINS

This application is a continuation-in-part of Ser. No. 08/476,110, filed on Jun. 6, 1995, presently abandoned.

FIELD OF THE INVENTION

The present invention relates to a novel family of purified proteins, and compositions containing such proteins, which compositions are useful for the induction of cartilaginous tissue formation, wound healing and cartilage and other tissue repair. These proteins may also be used in compositions for augmenting the activity of bone morphogenetic proteins. In particular, the present application also relates to the use of the above proteins for the induction of cartilaginous tissue, such as articular cartilage.

BACKGROUND OF THE INVENTION

The search for the molecule or molecules responsible for formation of bone, cartilage, tendon and other tissues present in bone and other tissue extracts has led to the discovery of a novel set of molecules called the Bone Morphogenetic Proteins (BMPs). The structures of several proteins, designated BMP-1 through BMP-13, have previously been elucidated. The unique inductive activities of these proteins, along with their presence in bone, suggests that they are important regulators of bone repair processes, and may be involved in the normal maintenance of bone tissue. There is a need to identify additional proteins which play a role in forming other vital tissues. Recently, the BMP-12-related subfamily of proteins, including BMP-13, was shown to have tendon/ligament-like tissue inducing activity, and to be useful in compositions for the induction of tendon/ligament-like tissue formation and repair. Surprisingly, the present inventors have found that members of this subfamily are also effective for the induction of cartilaginous tissue, and thus are useful for the treatment of diseases or defects of cartilaginous tissue. In particular, the inventors have found that BMP-13 or VL-1 is particularly effective for the induction of cartilaginous tissue. In addition, the inventors have found that BMP-9 is useful for increasing proteoglycan matrix synthesis, and is therefore useful for the maintenance of cartilaginous tissue.

SUMMARY OF THE INVENTION

The present invention relates to the use of proteins in the BMP-12 related subfamily of proteins for the induction of cartilaginous tissue, such as articular cartilage, the meniscus, and the articular surfaces of developing bone, or for the treatment of diseases or defects of cartilaginous tissue. In a preferred embodiment of the present invention, the protein used is BMP-13 or VL-1. This murine version of this protein has also been described as GDF-6.

BMP-12 related proteins are a subset of the BMP/TGF-β/Vg-1 family of proteins, including BMP-12 and BMP-13, which have previously been shown to have tendon/ligament-like tissue inducing ability, and which are encoded by DNA sequences which have been cloned and identified, e.g., using PCR. This subfamily also includes MP52, which is described in WO93/16099. The BMP-12-related family of proteins, the DNA sequences encoding them, vectors, host cells, compositions and methods of making the proteins have all been extensively described in WO95/16035, as well as Ser. No. 08/362,670, filed on Dec. 22, 1994, now U.S. Pat. No. 5,658,882; 08/333,576, filed on Nov. 2, 1994, and 08/217,780, filed Mar. 25, 1994, now abandoned; all of these applications are continuations-in-part of 08/164,103, filed on Dec. 7, 1993, presently abandoned. The disclosures of these applications are hereby incorporated herein by reference.

In the present invention, compositions containing a BMP-12 related protein, preferably BMP-13 or VL-1, are administered to a patient in need of cartilage repair, or having a disease or defect involving cartilaginous tissue, such as osteoarthritis.

The DNA molecules preferably have a DNA sequence encoding the BMP-13 protein, the sequence of which is provided in WO95/16035. The DNA molecules encoding BMP-13 protein, host cells and vectors and methods of making BMP-13 are also described in WO95/16035. The disclosure of that document is hereby incorporated by reference herein.

BMP-12, and other proteins in the related subfamily, such as BMP-13, have previously been characterized by the ability to induce the formation of tendon/ligament-like tissue. The present inventors have shown that members of the BMP-12-related family of proteins, preferably BMP-13, may further be characterized by the ability to induce formation of cartilaginous tissue. In a preferred embodiment, the purified polypeptide may be in the form of a dimer comprised of two subunits, each with the amino acid sequence of BMP-13.

In another embodiment, the present invention comprises compositions comprising an effective amount of the above-described BMP-12 related proteins, preferably BMP-13. In the compositions, the protein may be admixed with a pharmaceutically acceptable vehicle. In a particular embodiment, the composition may additionally include one or more additional transforming growth factor-β proteins or BMPs proven to be osteogenic, preferably BMP-2, -4, -5, -6 and/or BMP-7; more preferably BMP-2, -4 or BMP-7. The composition comprising both a BMP-12 related protein and another TGF-β or BMP may be useful for the regeneration of multiple tissue types, for example, at the interface or junction between tissues. The composition comprising both a protein which is useful for the induction of chondrocytes and cartilaginous tissue, such as BMP-12, BMP-13 or BMP52 and a protein useful for the induction of osteocytes and bone tissue, such as BMP-2, -4, -5, -6 or BMP-7 may be especially useful for the treatment of articular cartilage, in which the articular surface, cartilage, subchondral bone and/or tidemark interface between cartilage and bone may need to be repaired. A good source of osteocytes and chondrocytes for repair of the subchondral bone, tidemark interface and cartilage tissue may be obtained using the combination of factors. The most preferred of such embodiments is a composition combining BMP-2 and BMP-13.

In another preferred embodiment of the present invention, the composition comprises both a protein which is useful for the induction of chondrocytes or cartilaginous tissue, such as BMP-12, MP52 or BMP-13, together with a protein which is useful for the maintenance of chondrocytes, or cartilaginous tissue, such as BMP-9 and, to a lesser degree, BMP-2, BMP-4 and BMP-7. The composition comprising BMP-13 and BMP-9 may be especially useful for the induction and maintenance of cartilaginous tissue at a site in need of cartilage repair, such as an articular cartilage defect. BMP-9 has been shown to be useful in the maintenance of mature chondrocytes. Thus, in a preferred embodiment of the present invention, a protein useful for the induction of chondrocytes or cartilaginous tissue, such as BMP-13, BMP-12 or MP52 may be applied first, in order to induce the formation of chondrocytes, and BMP-9 or other suitable factor, such as BMP-2, BMP-4 or BMP-7, administered at a later time, in order to maintain the chondrocytes and cartilage tissue thus formed. The BMP-13 and BMP-9 may also be administered in a single composition. Such a composition is preferably administered in a form which allows for release of BMP-13 prior to release of BMP-9, so that the cartilage-induction effect of BMP-13 precedes the cartilage-maintenance effect of BMP-9.

In another preferred embodiment, the composition comprises at least one protein which is useful for the induction of cartilaginous tissue, such as BMP-13, BMP-12 or MP-52; one protein which is able to induce formation of subchondral bone tissue, such as BMP-2, -4 or -7; and one protein useful for the maintenance of cartilaginous tissue, such as BMP-9. The most preferred of such compositions comprises BMP-13, BMP-2 and BMP-9; or BMP-13, BMP-7 and BMP-9.

The present invention also includes methods for cartilaginous tissue healing and tissue repair, for treating osteoarthritis, or other cartilage defects, and for inducing cartilaginous tissue formation in a patient in need of same, comprising administering to said patient an effective amount of the above composition. The invention also includes heterodimeric protein molecules comprising one monomer having the amino acid sequence of a protein which is useful for the induction of chondrocytes or cartilaginous tissue, preferably BMP-13, and one monomer having the amino acid sequence of another protein of the TGF-β subfamily.

Finally, the present invention comprises methods for inducing cartilaginous tissue formation in a patient in need of same comprising administering to said patient an effective amount of a composition comprising a protein which exhibits the ability to induce formation of cartilaginous tissue, such as BMP-13, BMP-12 and MP-52, most preferably BMP-13. In a preferred embodiment, this method comprises administering to said patient simultaneously or subsequently an effective amount of a composition protein selected from the group consisting of comprising BMP-9, BMP-2, BMP-4 or BMP-7, most preferably BMP-9.

DETAILED DESCRIPTION OF THE INVENTION

The methods of inducing the formation of cartilaginous tissue are described further below. The DNA sequences further useful for isolating and cloning further DNA sequences encoding BMP-12 related proteins with similar activity. These BMP-12 related proteins may be homologues from other species, or may be related proteins within the same species.

As described previously, BMP-12 related proteins are a subset of the BMP/TGF-β/Vg-1 family of proteins, including BMP-12 and BMP-13, which have been previously been characterized by their tendon/ligament-like tissue inducing proteins encoded by DNA sequences which can be cloned and identified, e.g., using PCR, using BMP-12 specific primers reduced stringency conditions. In the present invention, it has also been shown that members of the BMP-12 related protein subfamily, particularly BMP-13 or GDF-6, are able to induce cartilaginous tissue formation.

The DNA encoding and amino acid sequences of BMP-12-related proteins, including BMP-13, are disclosed in WO95/16035, the disclosure of which is incorporated herein. The human MP52 DNA is described in WO93/16099, the disclosure of which is incorporated herein by reference. The MP52 protein is related to BMP-12 and BMP-13. However, WO93/16099 does not disclose the ability of the protein to form cartilaginous or tendon/ligament-like tissue, or its use in compositions for induction of cartilage or tendon/ligament-like tissue. Human MP52 was originally isolated using RNA from human embryo tissue. It is contemplated herein that MP52 may be useful in the compositions and methods of the present invention.

The DNA encoding and amino acid sequences of BMP-9 are disclosed in WO93/00432, the disclosure of which is incorporated herein by reference.

The method of the present invention employs proteins which are able to induce cartilaginous tissue or other tissue formation in circumstances where such tissue is not normally formed, and has application in the healing of cartilage, for example articular cartilage tears, deformities and other cartilage defects in humans and other animals. Such a preparation employing a cartilaginous tissue inducing protein may have prophylactic use in preventing damage to cartilaginous tissue, as well as use in the improved fixation of cartilage to bone or other tissues, and in repairing defects to cartilage tissue. De novo cartilaginous tissue formation induced by a composition of the present invention contributes to the repair of congenital, trauma induced, or other cartilage defects of other origin, and is also useful in surgery for attachment or repair of cartilage. The compositions of the invention may also be useful in the treatment of arthritis and other cartilage defects. The compositions of the present invention can also be used in other indications wherein it is desirable to heal or regenerate cartilage tissue. Such indications include, without limitation, regeneration or repair of injuries to the articular cartilage. The compositions of the present invention may provide an environment to attract cartilage-forming cells, stimulate growth of cartilage-forming cells or induce differentiation of progenitors of cartilage-forming cells.

By cartilaginous tissue, it is meant chondrocytes, and tissue which is formed by chondrocytes, which demonstrate the histological and compositional characteristics of cartilage. For example, tissue which exhibits the marker proteins characteristic of cartilage and/or chondrocytes, which are described further herein, such as type II collagen and aggrecan, also known as proteoglycan core protein.

The proteins useful in the methods of the present invention are capable of inducing the formation of cartilaginous tissue. These proteins may be further characterized by the ability to demonstrate cartilaginous tissue formation activity in the assays described below. It is contemplated that these proteins may have ability to induce the formation of other types of tissue, such as tendon and ligament, as well.

The cartilaginous tissue-inducing proteins provided herein also include factors encoded by the sequences similar to those of naturally-occurring BMP-12 related proteins, such as BMP-13, but into which modifications are naturally provided (e.g. allelic variations in the nucleotide sequence which may result in amino acid changes in the polypeptide) or deliberately engineered. Similarly, the cartilaginous tissue-maintaining proteins provided herein also include factors encoded by the sequences similar to those of naturally-occurring BMP-9 protein, but into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of BMP-13 and/or BMP-9. These sequences, by virtue of sharing primary, secondary, or tertiary structural and conformational characteristics with cartilaginous tissue growth or maintenance factor polypeptides of naturally-occurring BMP-13 or BMP-9 may possess cartilaginous or other tissue growth or maintenance factor biological properties in common therewith. Thus, they may be employed as biologically active substitutes for naturally-occurring cartilaginous tissue inducing polypeptides, and cartilaginous tissue maintenance polypeptides in therapeutic compositions and processes.

Other specific mutations of the sequences of cartilaginous tissue inducing proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences may be asparagine-X-threonine, asparagine-X-serine or asparagine-X-cysteine, where X is usually any amino acid except proline. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of protein will also result in production of a non-glycosylated protein, even if the glycosylation sites are left unmodified.

The compositions for inducing cartilaginous tissue formation of the present invention may comprise an effective amount of a cartilaginous tissue inducing protein, wherein said protein comprises the amino acid sequence of BMP-13, as well as mutants and/or variants of BMP-13, which exhibit the ability to form cartilaginous tissue. Compositions of the present invention may further comprise additional proteins, such as additional members of the TGF-β superfamily of proteins, such as activins. Another aspect of the invention provides pharmaceutical compositions containing a therapeutically effective amount of a cartilaginous tissue-inducing protein, such as BMP-13 or VL-1, in a pharmaceutically acceptable vehicle or carrier. These compositions may be used to induce the formation of cartilaginous tissue or other tissue. It is contemplated that such compositions may also be used for articular cartilage repair, wound healing and other tissue repair, such as skin repair. It is further contemplated that proteins of the invention may increase neuronal survival and therefore be useful in transplantation and treatment of conditions exhibiting a decrease in neuronal survival. Compositions of the invention may further include at least one other therapeutically useful agent, such as the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; BMP-9, disclosed in PCT publication WO93/00432; BMP-10, disclosed in PCT application WO94/26893; and BMP-11, disclosed in PCT application WO94/26892. The disclosure of the above documents are hereby incorporated by reference herein.

In one particular embodiment of the invention, the compositions comprising a therapeutically effective amount of a cartilaginous tissue-inducing protein, such as BMP-13 or VL-1, together with a therapeutically effective amount of a cartilaginous tissue-maintaining protein, such as BMP-9. In such a composition, the BMP-9 protein is preferably encapsulated, or otherwise administered in a manner which allows for the cartilaginous tissue-maintaining activity of BMP-9 to begin simultaneously with and continue subsequent to the cartilaginous tissue-inducing activity. For example, the BMP-9 component may be encapsulated in a resorbable polymer delivery system, such as polylactic acid, polyglycolic acid or copolymers thereof, polyorthoesters, polyorthocarbonates, and other polymers. Suitable polymers are disclosed for example in EP 0145240, the disclosure of which is hereby incorporated by reference. Alternatively, BMP-9 may be encapsulated in liposomes for delivery simultaneously with BMP-13. For example, liposome delivery of TGF-β protein is described in U.S. Pat. Nos. 5,206,023, 5,270,300; and 5,368,858, the disclosure of each of which are hereby incorporated by reference. Both of these delivery systems may be modified to provide for release of BMP-9 at a later time, or over a more sustained time period, allowing for the beneficial effects of BMP-9 on chondrocyte and cartilage maintenance to act complementary to the beneficial effects of BMP-9 on induction of chondrocytes and cartilaginous tissue.

The proteins or compositions of the present invention may also be useful for treating cell populations, such as embryonic cells or stem cell populations, to enhance or enrich the growth, differentiation and/or maintenance of the cells. The treated cell populations may be useful for gene therapy applications.

The compositions of the invention may comprise, in addition to a cartilaginous tissue-inducing protein such as BMP-13 or VL-1, other therapeutically useful agents including MP52, parathyroid hormone-related peptide (PTHrP); epidermal growth factor (EGF), fibroblast growth factor (FGF), platelet derived growth factor (PDGF), transforming growth factors (TGF-α and TGF-β), and fibroblast growth factor-4 (FGF-4), parathyroid hormone (PTH), leukemia inhibitory factor (LIF/HILDA/DIA), insulin-like growth factors (IGF-I and IGF-II). Portions of these agents may also be used in compositions of the present invention. For example, a composition comprising both BMP-2 and BMP-13 implanted together may give rise to both bone and cartilaginous tissue. Such a composition may be useful for treating defects of the junction between cartilage, and bone form simultaneously at contiguous anatomical locations, and may be useful for regenerating tissue at the site of cartilage attachment to bone. Compositions including PTHrP may also be of particular interest because it has been found that this factor is useful in maintaining chondrocytic phenotype of cells. See co-pending patent application Ser. No. 08/622,101, filed on Mar. 26, 1996, the disclosure of which is hereby incorporated by reference. Thus, the compositions of the present invention include combinations of PTHrP with the cartilage-inducing and/or cartilage-maintaining proteins of the present invention.

It is contemplated that the compositions of the invention may also be used in wound healing, such as skin healing and related tissue repair. The types of wounds include, but are not limited to burns, incisions and ulcers. (See, e.g. PCT Publication WO84/01106 for discussion of wound healing and related tissue repair).

It is expected that the proteins of the invention may act in concert with or perhaps synergistically with other related proteins and growth factors. Further therapeutic methods and compositions of the invention therefore comprise a therapeutic amount of at least one protein of the invention with a therapeutic amount of at least one of the BMP proteins described above. Such compositions may comprise separate molecules of the BMP proteins or heteromolecules comprised of different BMP moieties. For example, a method and composition of the invention may comprise a disulfide linked dimer comprising a BMP-12 related protein subunit and a subunit from one of the "BMP" proteins described above. Thus, the present invention includes compositions comprising a purified BMP-12 related polypeptide which is a heterodimer wherein one subunit comprises the amino acid sequence of BMP-13, and one subunit comprises an amino acid sequence for a bone morphogenetic protein selected from the group consisting of BMP-1, BMP-2, BMP-3, BMP-4, BMP-5, BMP-6, BMP-7, BMP-8, BMP-9, BMP-10 and BMP-11. A further embodiment may comprise a heterodimer of two disulfide bonded cartilaginous tissue inducing moieties such as BMP-12, VL-1 (BMP-13) or MP52. For example the heterodimer may comprise one subunit comprising the amino acid sequence of BMP-13, and the other subunit may comprise the amino acid of BMP-12. Further, compositions of the present invention may be combined with other agents beneficial to the treatment of the defect, wound, or tissue in question.

The preparation and formulation of such physiologically acceptable protein compositions, having due regard to pH, isotonicity, stability and the like, is within the skill of the art. The therapeutic compositions are also presently valuable for veterinary applications due to the lack of species specificity in TGF-β proteins. Particularly domestic animals and thoroughbred horses in addition to humans are desired patients for such treatment with the compositions of the present invention.

The therapeutic method includes administering the composition topically, systemically, or locally as an injectable and/or implant or device. When administered, the therapeutic composition for use in this invention is, of course, in a pyrogen-free, physiologically acceptable form. Further, the composition may desirably be encapsulated or injected in a viscous form for delivery to the site of tissue damage. Topical administration may be suitable for wound healing and tissue repair. Therapeutically useful agents other than the proteins which may also optionally be included in the composition as described above, may alternatively or additionally, be administered simultaneously or sequentially with the composition in the methods of the invention. In addition, the compositions of the present invention may be used in conjunction with presently available treatments for cartilage injuries, such as suture (e.g., vicryl sutures or surgical gut sutures, Ethicon Inc., Somerville, N.J.) or cartilage allograft or autograft, in order to enhance or accelerate the healing potential of the suture or graft. For example, the suture, allograft or autograft may be soaked in the compositions of the present invention prior to implantation. It may also be possible to incorporate the protein or composition of the invention onto suture materials, for example, by freeze-drying.

The compositions may include an appropriate matrix and/or sequestering agent as a carrier. For instance, the matrix may support the composition or provide a surface for cartilaginous tissue formation and/or other tissue formation. The matrix may provide slow release of the protein and/or the appropriate environment for presentation thereof. The sequestering agent may be a substance which aids in ease of administration through injection or other means, or may slow the migration of protein from the site of application.

The choice of a carrier material is based on biocompatibility, biodegradability, mechanical properties, cosmetic appearance and interface properties. The particular application of the compositions will define the appropriate formulation. Potential matrices for the compositions may be biodegradable and chemically defined. Further matrices are comprised of pure proteins or extracellular matrix components. Other potential matrices are non-biodegradable and chemically defined. Preferred matrices include collagen-based materials, including sponges, such as Helistat® (Integra LifeSciences, Plainsboro, N.J.), or collagen in an injectable form, as well as sequestering agents, which may be biodegradable, for example hyaluronic acid derived. Biodegradable materials, such as cellulose films, or surgical meshes, may also serve as matrices. Such materials could be sutured into an injury site, or wrapped around the cartilage.

Another preferred class of carrier are polymeric matrices, including polymers of poly(lactic acid), poly(glycolic acid) and copolymers of lactic acid and glycolic acid. These matrices may be in the form of a sponge, or in the form of porous particles, and may also include a sequestering agent. Suitable polymer matrices are described, for example, in WO93/00050, the disclosure of which is incorporated herein by reference.

Preferred families of sequestering agents include blood, fibrin clot and/or cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the activity of the progenitor cells.

Additional optional components useful in the practice of the subject application include, e.g. cryogenic protectors such as mannitol, sucrose, lactose, glucose, or glycine (to protect the protein from degradation during lyophilization), antimicrobial preservatives such as methyl and propyl parabens and benzyl alcohol; antioxidants such as EDTA, citrate and BHT (butylated hydroxytoluene); and surfactants such as poly(sorbates) and poly(oxyethylenes); etc.

As described above, the compositions of the invention may be employed in methods for treating a number of cartilage defects, such as the regeneration of cartilaginous tissue in areas of cartilage damage, to assist in repair of tears of cartilage tissue, and various other types of tissue defects or wounds. These methods, according to the invention, entail administering to a patient needing such cartilaginous tissue or other tissue repair, a composition comprising an effective amount of a cartilaginous tissue inducing protein, such as described in WO95/16035, the disclosure of which is hereby incorporated by reference. These methods may also entail the administration of a cartilaginous tissue inducing protein in conjunction with at least one of the BMP proteins described above.

In another embodiment, the methods may entail administration of a heterodimeric protein in which one of the monomers is a cartilaginous tissue inducing polypeptide, such as BMP-12, VL-1 (BMP-13) or MP52, and the second monomer is a member of the TGF-β superfamily of growth factors. In addition, these methods may also include the administration of a cartilaginous tissue inducing protein with other factors including PTHrP, EGF, FGF, TGF-α, TGF-β, and IGF.

Thus, a further aspect of the invention is a therapeutic method and composition for repairing cartilaginous tissue, for repairing cartilage as well as treating arthritis and other conditions related to arthritis defects. Such compositions comprise a therapeutically effective amount of one or more cartilaginous tissue inducing proteins, such as BMP-13, in admixture with a pharmaceutically acceptable vehicle, carrier or matrix.

The dosage regimen will be determined by the attending physician considering various factors which modify the action of the composition, e.g., amount of cartilaginous tissue desired to be formed, the site of cartilaginous tissue damage, the condition of the damaged cartilaginous tissue, the size of a wound, type of damaged tissue, the patient's age, sex, and diet, the severity of any infection, time of administration and other clinical factors. The dosage may vary with the type of matrix used in the reconstitution and the types of additional proteins in the composition. The addition of other known growth factors, such as IGF-I (insulin like growth factor I), to the final composition, may also affect the dosage. In general, the amount of recombinant BMP protein useful for inducing formation of cartilaginous tissue will be in an amount of about 1 to about 100 ug for a defect of approximately 3 mm×3 mm in size. In general, the amount of recombinant BMP protein useful for inducing maintenance of cartilaginous tissue will be in an amount of about 1 to about 1000 ng per ml of solution.

Progress can be monitored by periodic assessment of cartilaginous tissue formation, or cartilaginous tissue growth and/or repair. The progress can be monitored by methods known in the art, for example, X-rays, arthroscopy, histomorphometric determinations and tetracycline labeling.

The following examples illustrate practice of the present invention in recovering and characterizing human cartilaginous tissue inducing protein and employing them to recover the other cartilaginous tissue inducing proteins, obtaining the human proteins, expressing the proteins via recombinant techniques, and demonstration of the ability of the compositions of the present invention to form cartilaginous tissue in an in vivo model. Although the examples demonstrate the invention with respect to BMP-13 as the cartilage-inducing protein, with minor modifications within the skill of the art, the same results may be attainable with other proteins with the effect of inducing formation of cartilaginous tissue, particularly BMP-12 or MP52. Although the examples demonstrate the invention with respect to BMP-2 as the osteogenic protein, with minor modifications within the skill of the art, the same results may be attainable with other proteins with the effect of inducing the formation of osteocytes and bone tissue, particularly BMP-4 or BMP-7.

EXAMPLE 1

Localization of BMP-13 mRNA During Embryogenesis

BMP-13 specific ribonucleotide probes were used to localize the expression of BMP-13 mRNA transcripts during mouse embryogenesis. When compared to the osteogenic protein, BMP-2, BMP-13 mRNAs exhibit a more restricted pattern of expression. In the developing limb, BMP-13 transcripts are observed only in the region between developing articular cartilage surfaces, and not in the cartilage condensations where transcripts for BMP-2 receptors are evident, or in the interdigital mesenchyme where BMP-2 and BMP-4 mRNA transcripts are abundant.

EXAMPLE 2

Cartilage Induction Using BMP-13

BMP-13 was tested for its effect on cell lines derived from E13 mouse limb buds. Cells are grown to confluence on medium containing DME supplemented with 1% fetal calf serum. The cells are treated with BMP-13 in varying doses from less than 1 ng/ml up to about $5.0 \times 10^3$ ng/ml. Effects are seen with doses of at least about 0.1 ng/ml. After 10 days of treatment with BMP-13, a chondroblast-like phenotype with an accumulation of proteoglycan-rich matrix around the cells. Northern analysis of mRNA from BMP-13 treated limb bud cells revealed expression of both type II collagen and proteoglycan core protein, but not osteocalcin. Type II collagen and proteoglycan core protein are known markers for chondroblasts, or cartilaginous tissue.

As a control, similar treatment with BMP-2, a known osteogenic protein, results in the expression of a bone phenotype characterized by the production of osteocalcin, alkaline phosphatase and type I collagen. Osteocalcin, alkaline phosphatase and type I collagen are known markers for osteoblasts, or bone tissue.

These observations, combined with the localization of BMP-13 during limb development support the conclusion that BMP-13 is involved in induction of cartilaginous tissue, and more particularly in cartilage formation that occurs at the articular surfaces of developing bones.

EXAMPLE 3

Northern Analysis

Using Northern analysis, BMP-13 and other proteins can be tested for their effects on various cell lines. Suitable cell lines include cell lines derived from E13 mouse limb buds. After 10 days of treatment with BMP-13 or other protein, the cell phenotype is examined histologically for indications of tissue differentiation. In addition, Northern analysis of mRNA from BMP-13 or other protein treated cells can be performed for various markers including one or more of the following markers for bone, cartilage and/or tendon/ligament, as described in Table I:

TABLE I

| Marker | Bone | Cartilage | Tendon/Ligament |
|---|---|---|---|
| Osteocalcin | + | − | − |
| Alkaline Phosphatase | + | − | − |
| Proteoglycan Core Protein | +/−[1] | + | +[2] |
| Collagen Type I | + | + | + |
| Collagen Type II | +/−[1] | + | +[2] |
| Decorin | + | + | + |
| Elastin | +/−[3] | ? | + |

[1]Marker seen early, marker not seen as mature bone tissue forms
[2]Marker depends upon site of tendon; strongest at bone interface
[3]Marker seen at low levels

EXAMPLE 4

Full Thickness Articular Cartilage Repair Model

A full thickness articular cartilage defect model in the femoral-patellar joint of adult rabbits is used to evaluate the ability of the BMPs to affect cartilage and bone repair. Adult New Zealand White rabbits are anesthetized and prepared for sterile surgery. A 3×3 mm defect through articular cartilage and into underlying subchondral bone is drilled into the patellar groove of the knee joint. The defect is either left empty (empty control), filled with collagen sponge (collagen control), or with collagen sponge soaked with rhBMP-13 protein, another BMP protein, or a combination of BMP-13 and other BMPs (experimental). The incision is closed and animals are allowed free movement within their cages for 4 weeks. After 4 weeks the animals are humanely euthanized and the articular cartilage/subchondral bone defect is evaluated histologically for tissue architecture, quantity and quality of repair tissue.

In one experiment, defects were filled with (1) 10 ug of rhBMP-13; (2) 5 ug rhBMP-2; or (3) 2.5 ug rhBMP-2 plus 5 ug rhBMP-13 combined on a collagen sponge [rhBMP-2/13]. Four weeks post-operatively, repair tissues were evaluated histologically using a grading system modified from Wakatani et al., *J. Bone and Joint Surg.*, 76-A:4 (1994). Total histological scores demonstrated significant differences between all BMP treated groups relative to empty or collagen controls. Morphologically, the repair cartilage resulting from treatment with rhBMP-13 or rhBMP-2/13 was different than that resulting from treatment with rhBMP-2 alone. Thirty percent of the defects containing rhBMP-13 had an organization of chondrocytes in the repair cartilage similar to normal hyaline articular cartilage radial zone architecture, a phenotype not seen with rhBMP-2 treatment at 4 weeks. Defects treated with rhBMP-2 alone repaired with fibrocartilage rather than hyaline-like cartilage. However, this cartilage consistently lacked the holes and fissures regularly observed in empty or collagen controls. This improved repair may reflect the rapid and reproducible subchondral bone healing in defects exposed to rhBMP-2. Subchondral bone repair was significantly improved ($p<0.05$) in defects treated with rhBMP-2 and rhBMP-2/13 (88% and 90% replacement, respectively) as compared to empty or collagen controls, or defects treated with rhBMP-13 alone (53%, 55%, and 51% replacement, respectively). These results demonstrate the differential effects of rhBMP-2 and rhBMP-13 on the early repair of fill-thickness articular cartilage defects. The beneficial effects of rhBMP-2 on cartilage repair appear to stem from its ability to rapidly and consistently reproduce the subchondral bone plate, resulting in a stable site for chondrogenesis, while the beneficial effects of rhBMP-13 are more directly related to repairing articular cartilage with little osteogenic effect, and results in a cartilage which more closely resembles normal hyaline articular cartilage in its cellular organization. The combined beneficial effects of these two proteins results in consistent subchondral bone repair with a significant percentage of repair tissue demonstrating the hyaline cartilage-like phenotype.

EXAMPLE 5

Modulation of Matrix Synthesis by BMPs

Articular cartilage was shaved from calf carpal joints and digested in 0.2% collagenase to release the chondrocytes. The chondrocytes were maintained in DME with 50 ug/mL ascorbate, 6 mM glutamine, antibiotics, and supplemented with 10% FCS for 21 days. The initial cell density was $0.125 \times 10^6$ cells/mL. Cytokines were added to the cultures at concentrations previously shown to induce near maximal response. Total DNA and proteoglycan content were measured using spectrophotometric assays on Day 1, 2, 6, 8, 10, 12, 14, and 21 cultures. Histology of the cell layers was performed on Day 14 samples and the slides were stained for proteoglycan content using Safranin-O.

Results: rhBMP-2, rhBMP-9 and TGF-β1 stimulated proteoglycan synthesis significantly above control levels after 14 days in culture ($p<0.05$). Further, after 21 days in culture, rhBMP-9 treatment increased proteoglycan levels significantly more than control, rhBMP-2 or TGF-β1 treatment. rhBMP-9 and TGF-β1 significantly increased the rate of increase of cell number, as measured by DNA content, when compared to empty control cultures ($p<0.05$). Histologically, the empty cultures showed minimal extracellular matrix synthesis by Safranin-O staining. The TGF-β1 treated cultures contained more cells, but they were not morphologically similar to chondrocytes. Safranin-O staining demonstrated a marked increase in proteoglycan production in rhBMP-9 treated cultures, with rhBMP-2 treatment increasing proteoglycan synthesis of a sub-population of cells.

The observation that rhBMP-2 and rhBMP-9 stimulate proteoglycan synthesis in culture indicate that these factors play a role in adult articular cartilage metabolism. The ability of these cytokines to stimulate matrix synthesis by articular chondrocytes and maintain chondrocyte phenotype suggest important applications including cartilage defect repair and prevention/reversal of osteoarthritis, chondrocyte phenotype. These studies suggest that these BMPs may be particularly useful for cartilage differentiation, growth, maintenance and repair in conjunction with rhBMP-13, which has shown the ability to cause chondrocyte differentiation.

EXAMPLE 6

Stimulation of Articular Cartilage Metabolism by rhBMP-9 and rhBMP-2

$5 \times 1$ mm diameter cartilage discs were cut from the metacarpophalangeal joints of 7–10 day old calves immediately after euthanasia. After three days of equilibration, the explants were incubated in serum free medium with increasing doses of TGF-β1, rhBMP-2 or rhBMP-9. Medium and cytokine were changed daily. After three days in culture, 10 $\mu Ci^{35}SO_4$/ml was added for eight hours. Explants were harvested and the radiolabeled proteoglycans quantified after column chromatography of tissue digests. Newly synthesized proteoglycan was normalized to the DNA content of the explant. Total proteoglycan accumulation in the cartilage matrix was also evaluated. Explants were allowed to incubate with or without cytokine for 14 days and evaluated for total proteoglycan and DNA content. Proteoglycan content was evaluated using a spectrophotometric assay and DNA content using the Hoechst dye binding assay. All results are the mean of six trials.

Results: Explants treated with 10, 100 and 1,000 ng rhBMP-9/ml showed a significant increase in proteoglycan synthesis after three days in culture. 100 or 1,000 ng rhBMP-2/ml also increased proteoglycan synthesis. In contrast, proteoglycan synthesis by explants treated with TGF-β1 did not increase above untreated levels. In fact, 100 ng/ml TGF-β1 significantly inhibited proteoglycan synthesis below that of untreated explants. Total proteoglycan content of rhBMP-9 treated explants increased to 1.45–2.1 times untreated explants after 14 days in culture, with a maximal increase at a dose of 10 ng/ml. Content was significantly higher than untreated explants at all does ($p<0.05$). rhBMP-2 increased total proteoglycan content 1.46–1.91 times untreated explants, with maximal increase at 1,000 ng/ml. Content was significantly higher than untreated explants at 10 to 1,000 ng/ml ($p<0.05$). Proteoglycan content of TGF-β1 treated explants did not change during the culture period. DNA content of the rhBMP-9 and rhBMP-2 treated explants increased in a manner parallel to, but less pronounced than, the proteoglycan content.

The above results demonstrate that rhBMP-9 and rhBMP-2 increased proteoglycan synthetic rate and total matrix proteoglycan accumulation in bovine articular cartilage explants. This contrasted with the effects of TGF-β1 which inhibited proteoglycan synthesis. DNA content of the rhBMP-9 and rhBMP-2 treated explants also increased. These findings suggest both an increase in cell number and rate of synthesis per cell may be responsible for the increase in proteoglycan content. In all experiments, rhBMP-9 had a significant effect at lower doses than rhBMP-2. These results demonstrate that rhBMP-9 and rhBMP-2, particularly rhBMP-9, have the ability to increase DNA synthesis in differentiated chondrocytic cells, and thus may be effective inducers of chondrocyte or cartilaginous tissue maintenance.

EXAMPLE 7

Induction of Aggrecan Gene Expression and Synthesis in Articular Cartilage Explants by rhBMP-9.

Articular cartilage was harvested from the carpometacarpal joints of freshly killed calves and maintained in explant culture in DMEM supplemented with 1-glutamine, ascorbate, and 0.1% BSA. The cartilage was allowed to equilibrate for 48 hours, and to determine the dose-dependent response, the explants were then cultured, in triplicate, in the presence or absence of recombinant human BMP-9 (rhBMP-9)(0, 1, 10, 100, and 1,000 ng/ml) or IL-1 (10 ng/ml) for five days. To determine the time-dependent response, cartilage explants were cultured in the presence of 1,000 ng/ml for three, five, and seven days. For mRNA determinations, cartilage explants were then weighed and placed into 0.5 ml of Promega Total RNA Isolation System denaturing buffer [Chomczynski et al., $Anal.\ Biochem.,$ 162:156 (1987)], RNA was isolated, then purified (RNeasy RNA isolation kit), and reverse transcription was performed using oligo-dT primers [Re et al., $Anal.\ Biochem.$ 225:357 (1995)]. Non-competitive quantitative PCR was used to determine the mRNA levels for aggrecan [Id.]. The primers used were designed to amplify intron-spanning regions. The PCR products were analyzed by agarose gel electrophoresis with ethidium bromide staining, and band intensity was determined by image analysis. Quantitation was done by using standards consisting of known copy numbers of a plasmid containing, as insert, the specific PCR product. Results were expressed as copies per $\mu g$ total RNA. For $^{35}S$-sulfate incorporation studies, on day 5 explants were pulsed with 10 $\mu Ci$ $^{35}S$-sulfate for 12 hours. The cartilage was then digested with papain, and $^{35}S$-sulfate incorporation into glycosaminoglycan chains was determined. Statistical analysis was by ANOVA and Dunnens.

Results: The response of the cartilage explants to BMP-9 was dose-dependent. Control explants showed a level of aggrecan mRNA of $2.8\pm0.4\times10^8$ copies per $\mu g$ RNA. With increasing concentrations of BMP-9, there was a dose-dependent increase in the aggrecan mRNA levels. No change in aggrecan mRNA levels was detected at 1 and 10 ng/ml, but at 100 ng/ml and 1,000 ng/ml BMP-9 there was a significant stimulation of aggrecan mRNA levels ($p<0.05$). At 100 ng/ml there was a 1.9 fold increase in aggrecan mRNA levels, and at 1,000 ng/ml there was an increase of 6.5 fold compared to control levels. A time course study showed that maximal stimulation with 1,000 ng/ml was achieved within three days of incubation, and was maintained over seven days. $^{35}S$-sulfate incorporation was also increased by culture in the presence of BMP-9, and at 100 ng/ml the $^{35}S$-sulfate incorporate was increased by 2.7 fold. In contrast, explants cultured in the presence of 10 ng/ml IL-1 were found to have dramatically suppressed aggrecan mRNA levels, to <10% of controls ($p<0.05$). $^{35}S$-sulfate incorporation was also reduced, to 27% of the control incorporation.

Aggrecan is a major component of the extracellular matrix of articular cartilage, and is synthesized by chondrocytes. These results demonstrate that BMP-9 stimulates both the gene expression and synthesis of aggrecan in cartilage. Thus, BMP-9 may be effective for repair and maintenance of cartilage where stimulation of the synthesis of cartilage-specific matrix components is important.

What is claimed is:

1. A method for inducing articular cartilage tissue formation and maintenance comprising applying an effective amount of a composition to a site in need of articular cartilage repair, said composition consisting essentially of:
   (a) bone morphogenetic protein (BMP)-13; and
   (b) a cartilage maintenance-inducing protein selected from the group consisting of BMP-2, BMP-4, BMP-7 and BMP-9.

2. A method for the formation and maintenance of chondrocytes and cartilaginous tissue comprising applying an effective amount of a composition consisting essentially of:
   (a) BMP-13 protein; and
   (b) BMP-9 protein.

3. A method for the formation and maintenance of articular cartilaginous tissue and associated subchondral bone comprising applying an effective amount of a composition consisting essentially of:
   (a) BMP-13 protein;
   (b) BMP-9 protein; and
   (c) BMP-2 protein.

4. A method for the formation and maintenance of articular cartilagious tissue and associated subchondral bone comprising applying an effective amount of a composition consisting essentially of:
   (a) Bone morphogenetic Protein (BMP)-13 protein;
   (b) BMP-9 protein; and
   (c) BMP-7 protein.

5. A method for inducing articular cartilage tissue formation and maintenance comprising applying to a site in need of articular cartilage repair an effective amount of a composition comprising:
   (a) bone morphogenetic protein (BMP)-13;
   (b) an osteogenic protein selected from the group consisting of BMP-2, BMP-4, BMP-5, BMP-6 and BMP-7; and
   (c) BMP-9.

6. A method for inducing articular cartilage tissue formation and maintenance comprising applying to a site in need of articular cartilage repair an effective amount of a composition consisting essentially of:
   (a) bone morphogenetic protein (BPM)-13; and
   (b) BMP-9.

* * * * *